(12) United States Patent
Ward et al.

(10) Patent No.: US 7,433,727 B2
(45) Date of Patent: Oct. 7, 2008

(54) IMPLANTABLE BIOSENSOR

(75) Inventors: W. Kenneth Ward, Portland, OR (US); Michael D. Wood, Portland, OR (US)

(73) Assignee: Legacy Good Samaritan Hospital and Medical Center, Portland, OR (US)

( * ) Notice: Subject to any disclaimer, the term of this patent is extended or adjusted under 35 U.S.C. 154(b) by 234 days.

(21) Appl. No.: 10/948,954

(22) Filed: Sep. 24, 2004

(65) Prior Publication Data

US 2005/0107677 A1      May 19, 2005

Related U.S. Application Data

(60) Provisional application No. 60/505,931, filed on Sep. 24, 2003.

(51) Int. Cl.
*A61B 5/05*      (2006.01)
*A61B 5/00*      (2006.01)

(52) U.S. Cl. .................. 600/345; 600/347; 600/365

(58) Field of Classification Search .................. None
See application file for complete search history.

(56) References Cited

U.S. PATENT DOCUMENTS

| | | | |
|---|---|---|---|
| 5,165,407 A | | 11/1992 | Wilson et al. |
| 5,711,861 A | * | 1/1998 | Ward et al. .................. 600/347 |
| 5,741,330 A | | 4/1998 | Brauker et al. |
| 6,001,067 A | | 12/1999 | Shults et al. |
| 6,121,009 A | | 9/2000 | Heller et al. |
| 6,122,535 A | * | 9/2000 | Kaestle et al. .............. 600/322 |
| 6,212,416 B1 | | 4/2001 | Ward et al. |
| 6,233,471 B1 | * | 5/2001 | Berner et al. ................ 600/345 |
| 6,442,413 B1 | | 8/2002 | Silver |
| 6,466,810 B1 | | 10/2002 | Ward et al. |
| 6,477,395 B2 | | 11/2002 | Schulman et al. |
| 6,484,046 B1 | | 11/2002 | Say et al. |
| 6,512,939 B1 | | 1/2003 | Colvin et al. |
| 6,514,718 B2 | | 2/2003 | Heller et al. |
| 2001/0020137 A1 | * | 9/2001 | Granger ...................... 600/544 |
| 2002/0120186 A1 | * | 8/2002 | Keimel ........................ 600/365 |
| 2005/0043598 A1 | * | 2/2005 | Goode et al. ................. 600/316 |

OTHER PUBLICATIONS

Hu, W. J., J. W. Eaton, et al. (2001). "Molecular basis of biomaterial-mediated foreign body reactions." *Blood* 98(4): 1231-8.
Katou, F., H. Ohtnai, et al. (1998). "Procollagen-positive fibroblasts predominantly express fibrogenic growth factors and their receptors in human encapsulation process against foreign body." *J Pathol* 186(2): 201-8.
Khouw, I. M., P. B. van Wachem, et al. (1999). "TGF-beta and bFGF affect the differentiation of proliferating porcine fibroblasts into myofibroblasts in vitro." *Biomaterials* 20(19): 1815-22.
O'Connor, S. M., S. J. Patuto, et al. (1997). "Fibrinogen-dependent adherence of macrophages to surfaces coated with poly(ethylene oxide)/poly(propylene oxide) triblock copolymers." *Ann N Y Acad Sci* 831: 138-44.
Roberts, A. B., E. Piek, et al. (2001). "Is Smad3 a major player in signal transduction pathways leading to fibrogenesis?" *Chest* 120(1 Suppl): 43S-47S.
Updike, S. J., M. C. Shults, et al. (2000). "A subcutaneous glucose with improved longevity, dynamic range, and stability of calibration." *Diabetes Care* 23: 208-214.
Wolf, G., F. N. Ziyadeh, et al. (1995). "Angiotensin II-stimulated expression of transforming growth factor beta in renal proximal tubular cells: attenuation after stable transfection with the c-mas oncogen." *Kidney Int* 48(6): 1818-27.

* cited by examiner

*Primary Examiner*—Robert L. Nasser, Jr.
*Assistant Examiner*—Patricia C Mallari
(74) *Attorney, Agent, or Firm*—Kolisch Hartwell, P.C.

(57) ABSTRACT

The invention consists of a sensor with multiple indicating (sensing) electrodes covered with a selectively permeable membrane for monitoring fluid concentrations in a biological environment. The indicating electrodes respond to changes in certain analytes, such as glucose, through an enzyme-mediated reaction. The currents generated from the enzyme-mediated reactions are transmitted through radio signals to an external receiver where the information is processed and recorded. Through the use of various biomaterials and biochemicals associated with the sensor, the monitoring accuracy is improved and the overall viability is prolonged. The process of foreign body fibrosis (formation of a scar capsule around the implanted sensor) eventually limits the functional life of the device. We teach methods of delivery of certain biochemicals that can increase the functional life of the sensor by inhibiting the formation of the foreign body capsule or by stimulating the growth of capillaries into the capsule.

12 Claims, 5 Drawing Sheets

IMPLANTABLE BIOSENSOR

CROSS REFERENCE TO RELATED APPLICATIONS

This application claims priority under 35 U.S.C. § 119 and applicable foreign and international law and incorporates by reference in their entirety the following U.S. Provisional Patent Application Ser. No.60/505,931 filed Sep. 24, 2003.

This invention was made with Government support awarded by the National Institute of Health, (NIDDK, National Institute of Diabetes, Digestive Diseases, and Kidney Diseases) under grant no. RO1-DK59063; and National Institute of Health, (NIBIB, National Institute of Bioimaging and Bioengineering) under grant no. RO1-EB000743. The Government has certain rights in this invention.

This application also incorporates by reference in their entireties and for all purposes, the following U.S. Patents and Publications: U.S. Pat. Nos. 5,165,407; 5,711,861; 5,741,330; 6,001,067; 6,121,009; 6,212,416; 6,442,413; 6,466,810; 6,477,395; 6,484,046; 6,512,939; 6,514,718; Hu, W. J., J. W. Eaton, et al. (2001). "Molecular basis of biomaterial-mediated foreign body reactions." *Blood* 98(4): 1231-8; Katou, F., H. Ohtani, et al. (1998). "Procollagen-positive fibroblasts predominantly express fibrogenic growth factors and their receptors in human encapsulation process against foreign body." *J Pathol* 186(2): 201-8; Khouw, I. M., P. B. van Wachem, et al. (1999). "TGF-beta and bFGF affect the differentiation of proliferating porcine fibroblasts into myofibroblasts in vitro." *Biomaterials* 20(19): 1815-22; O'Connor, S. M., S. J. Patuto, et al. (1997). "Fibrinogen-dependent adherence of macrophages to surfaces coated with poly(ethylene oxide)/poly(propylene oxide) triblock copolymers." *Ann N Y Acad Sci* 831: 138-44; Roberts, A. B., E. Piek, et al. (2001). "Is Smad3 a major player in signal transduction pathways leading to fibrogenesis?" *Chest* 120(1 Suppl): 43S-47S; Rousseeuw, P. (1990). Robust Estimation and Identifying Outliers. *Statistical Methods for Engineers and Scientists*. W. HM. New York, McGraw-Hill, Inc: Chapter 16, pages 16.1-16.24; Updike, S. J., M. C. Shults, et al. (2000). "A subcutaneous glucose sensor with improved longevity, dynamic range, and stability of calibration." *Diabetes Care* 23: 208-214; Ward W K, Slobodzian E P, et al. (2002). "The Effect of Microgeometry, Implant Thickness and Polyurethane Chemistry on the Foreign Body Response to Subcutaneous Implants." *Biomaterials* 23: 4185-4192; Ward W K, C. H., Quinn M J, Federiuk I F, Wood M D (2003). "A Fully-Implantable Subcutaneous Glucose Sensor Array: Enhanced Accuracy from Multiple Sensing Units and a Median-based Algorithm." *Diabetes Technology and Therapeutics* (in press); and Wolf, G., F. N. Ziyadeh, et al. (1995). "Angiotensin II-stimulated expression of transforming growth factor beta in renal proximal tubular cells: attenuation after stable transfection with the c-mas oncogene." *Kidney Int* 48(6): 1818-27.

FIELD OF THE INVENTION

The invention consists of a sensor with multiple indicating electrodes coated with a selectively permeable membrane for monitoring fluid concentrations in a biological environment. Through the use of various biomaterials and biochemicals associated with the sensor, long-term sensing accuracy is achieved.

BACKGROUND OF THE INVENTION

Many fields of science require the monitoring of analyte concentrations in fluids. In an example of insulin-treated diabetes, afflicted persons must frequently monitor their blood glucose levels in order to appropriately ascertain the dose of insulin. Without an accurate measurement, insulin dosing would be dangerous.

Multiple devices have been devised for the measurement of analytes in fluid. Devices such as electrochemical sensors utilize electrodes coated with polymer membranes. The functions of such sensors can be manipulated depending on which materials are used and in what quantities so that necessary reactions are controlled. Depending on the reaction near the electrodes, changes in current can be measured and thus correlated to the analyte of interest.

The measurement of glucose in human blood makes use of electrochemical sensors. Sensors of this design measure blood glucose from samples drawn from a patient. In the case of diabetic patients, these samplings often occur several times per day. The sampling process, which equates to a finger prick, can be uncomfortable as well as difficult. Since blood sampling requires specially designed equipment, diabetic patients must have them readily available and thus carry their supplies with them at all times. Due to this cumbersome process, some patients fail to sample their blood as often as they should. Fortunately, an implantable glucose sensor would solve the problem of infrequent blood samplings.

Current implantable sensor designs have many problems that must be addressed before such a device can come to market. Constant subcutaneous or vascular access must be attained for a sensor to constantly measure glucose levels. Due to discomfort and the possibility of infection, wires protruding from the skin are undesirable. A completely implantable sensor that communicates with an external receiver through wireless transmission would solve this problem. Unfortunately, an implantable sensor could result in internal trauma if the sensor is especially large or inappropriately shaped. Also, a patient's body could interpret an implanted sensor as a foreign object and attempt to either destroy or isolate it. If either of these actions were successful, the analytes of interest could not be monitored. Sadly, all attempts thus far have failed in the long-term due to these issues.

SUMMARY OF THE INVENTION

The objectives stated above are achievable with the device and system of the present invention which includes a device for electrochemically sensing changes in the concentration of an analyte of interest.

In one embodiment of the invention, the device includes a lozenge-shaped sensor body with multiple sensing (indicating) electrodes and one reference electrode positioned on one side of a planar surface. The sensing (indicating) electrodes are covered by an enzyme layer including glucose oxidase and an outer selectively permeable membrane layer including carbonate polyurethane.

An implantable glucose sensor, according to the present invention, may be internally fitted with a transmitter which includes a power source (e.g. battery). The transmitter is capable of converting four current streams generated from the sensor into four corresponding coded radio signals. A processing receiver is positioned externally and used to receive and interpret the radio signals and thus yield analyte concentrations.

Biochemical compounds are described herein in the following definitions:

Analyte: a dissolved molecule of interest in a fluid environment

Anode: a negatively charged electrode when paired with a positively charged electrode Biomaterial: a material designed for use in a biological environment Biochemical: a chemical created for use in a biological environment Cathode: a positively charged electrode when paired with a negatively charged electrode Electrode: a conductive material consisting of either an anode or a cathode Indicating (sensing) electrode: an anode used in conjunction with a reference electrode Perm-selective membrane: a material capable of controlling the flow of certain molecules through it Reference electrode: a cathode used in conjunction with one or more anodes Receiver: a device capable of receiving radio signals Sensor: a device used to detect changes in analyte concentration Transmitter: a device capable of transmitting or sending radio signals

BRIEF DESCRIPTION OF DRAWINGS

FIG. 1 shows mean blood glucose and sensor glucose for near and distant units plotted as a function of time.

FIG. 2 shows a constant relationship between the lag duration and distance from the VEGF source.

FIG. 3 shows sensor accuracy in terms of the Mean Absolute Relative Difference (MARD), expressed as a percentage of blood glucose.

FIG. 4 shows the effect of local subcutaneous VEGF release using the Clarke Error Grid Analysis (EGA).

FIG. 5 shows individual data pairs for all sensing units immediately adjacent the VEGF source on a Clarke Error Grid.

DESCRIPTION OF THE INVENTION

Figure 1:
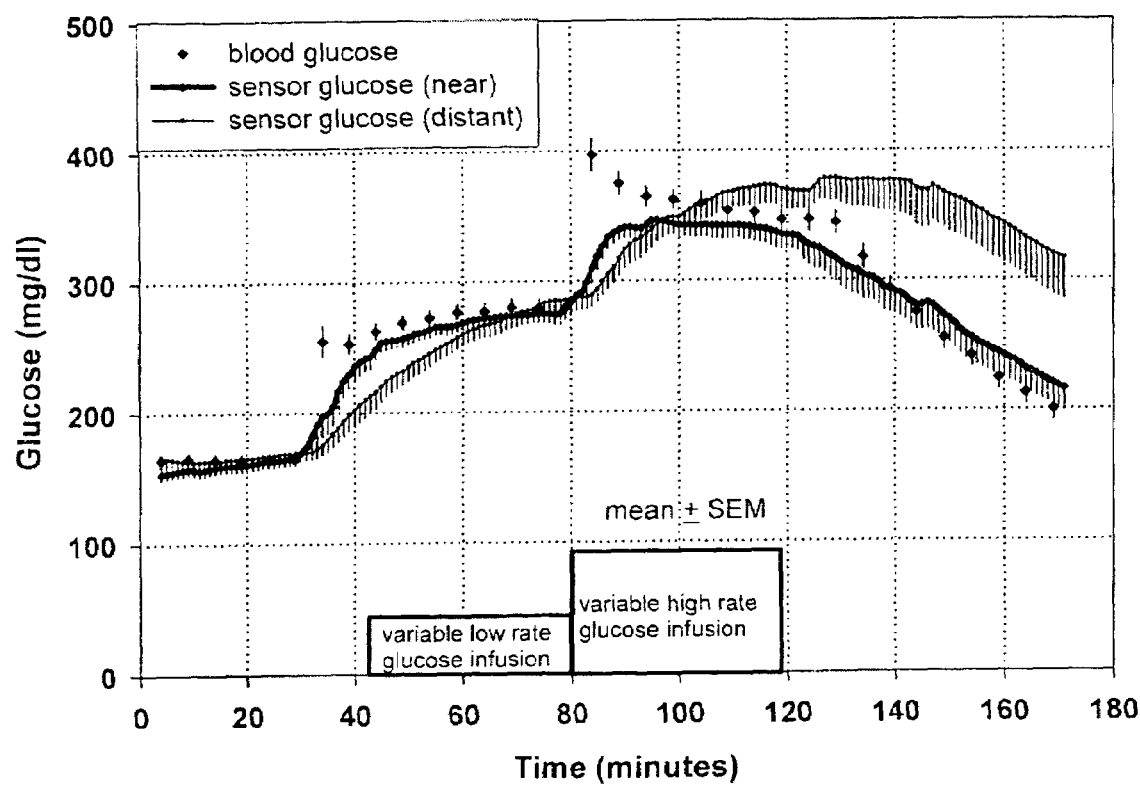
FIGS. 1-5 show the effect of VEGF in rats with functioning sensor arrays, wherein the indicating electrodes of the array are located at various distances from the infusion port.
Figure 2:
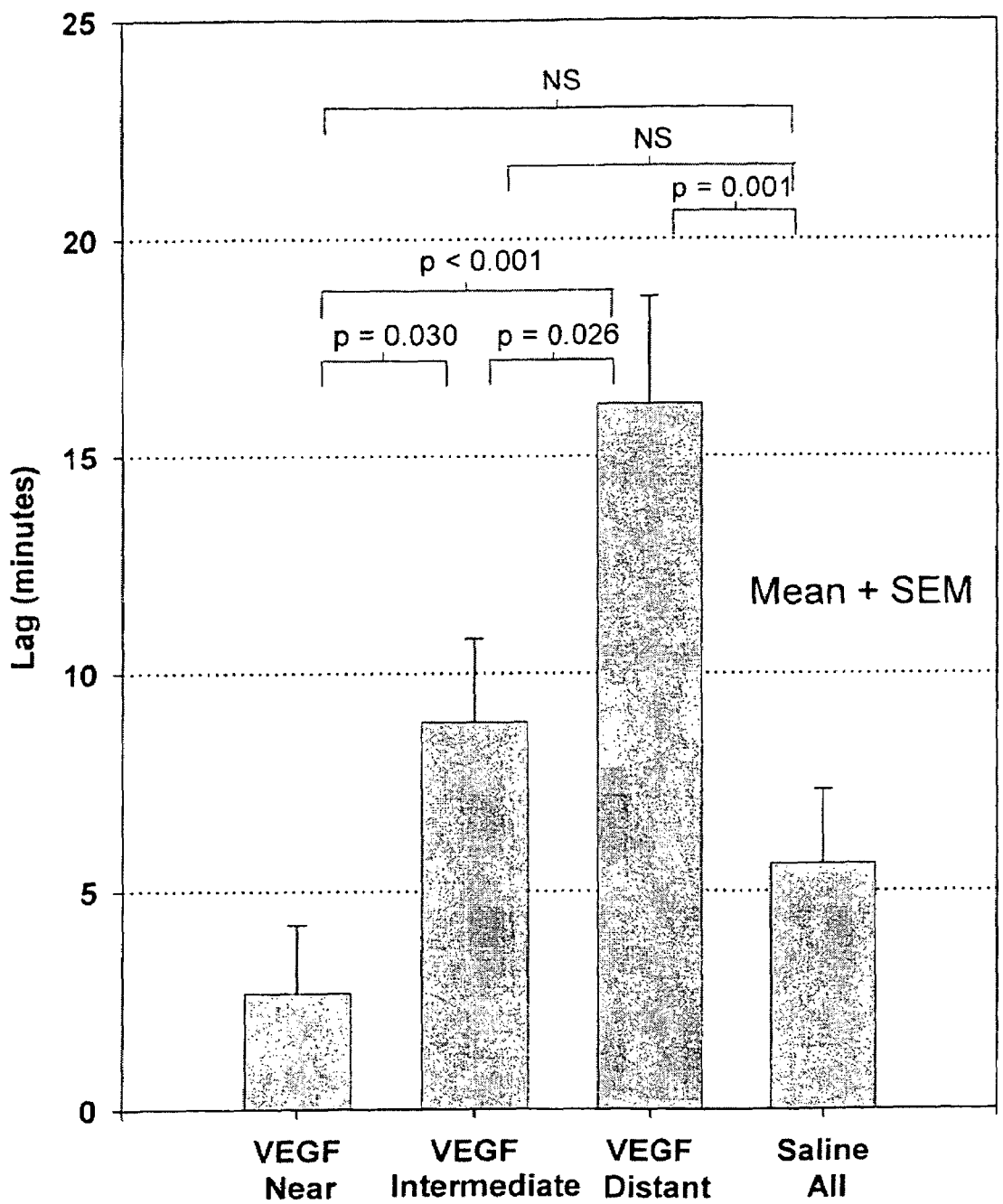
Figure 3:
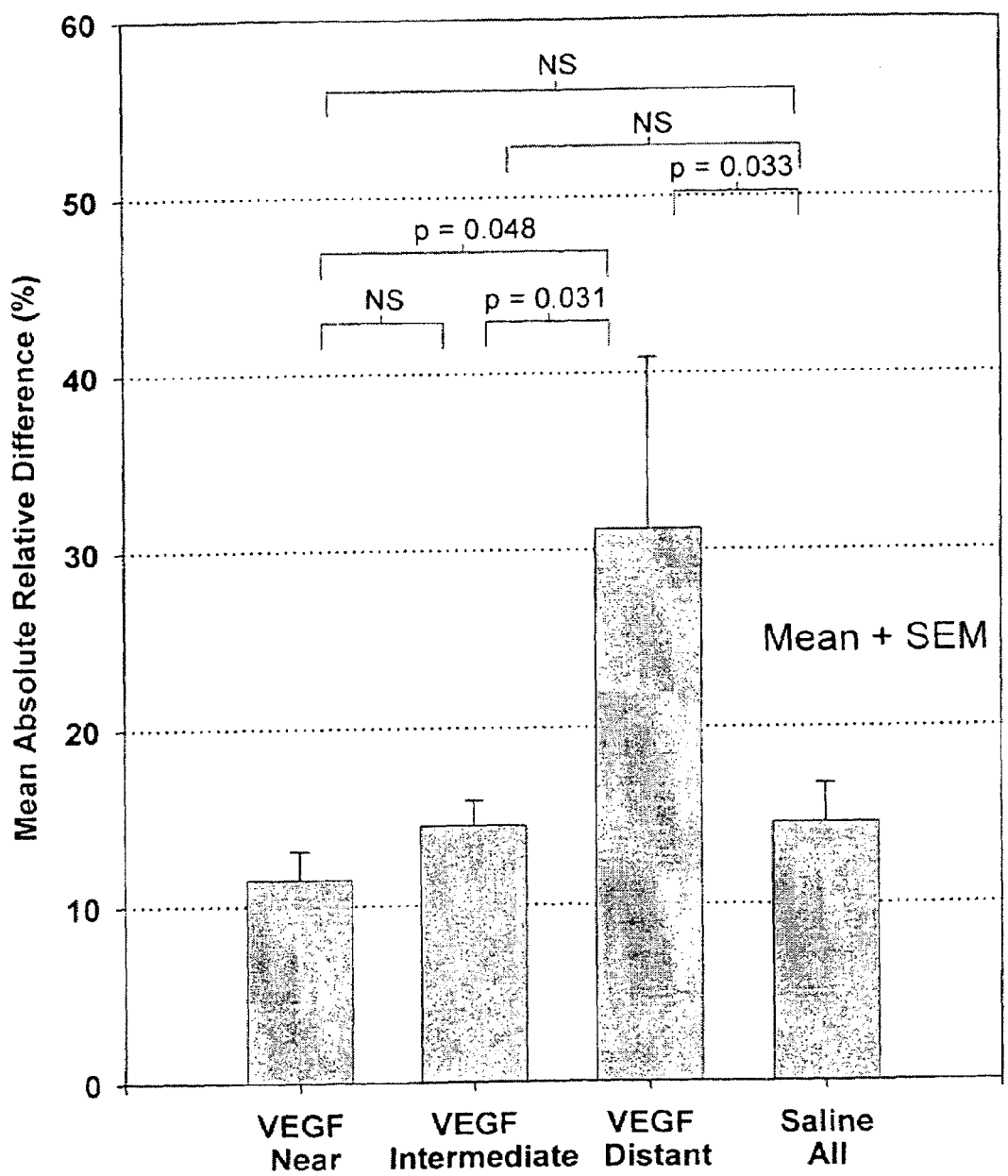
Figure 4:
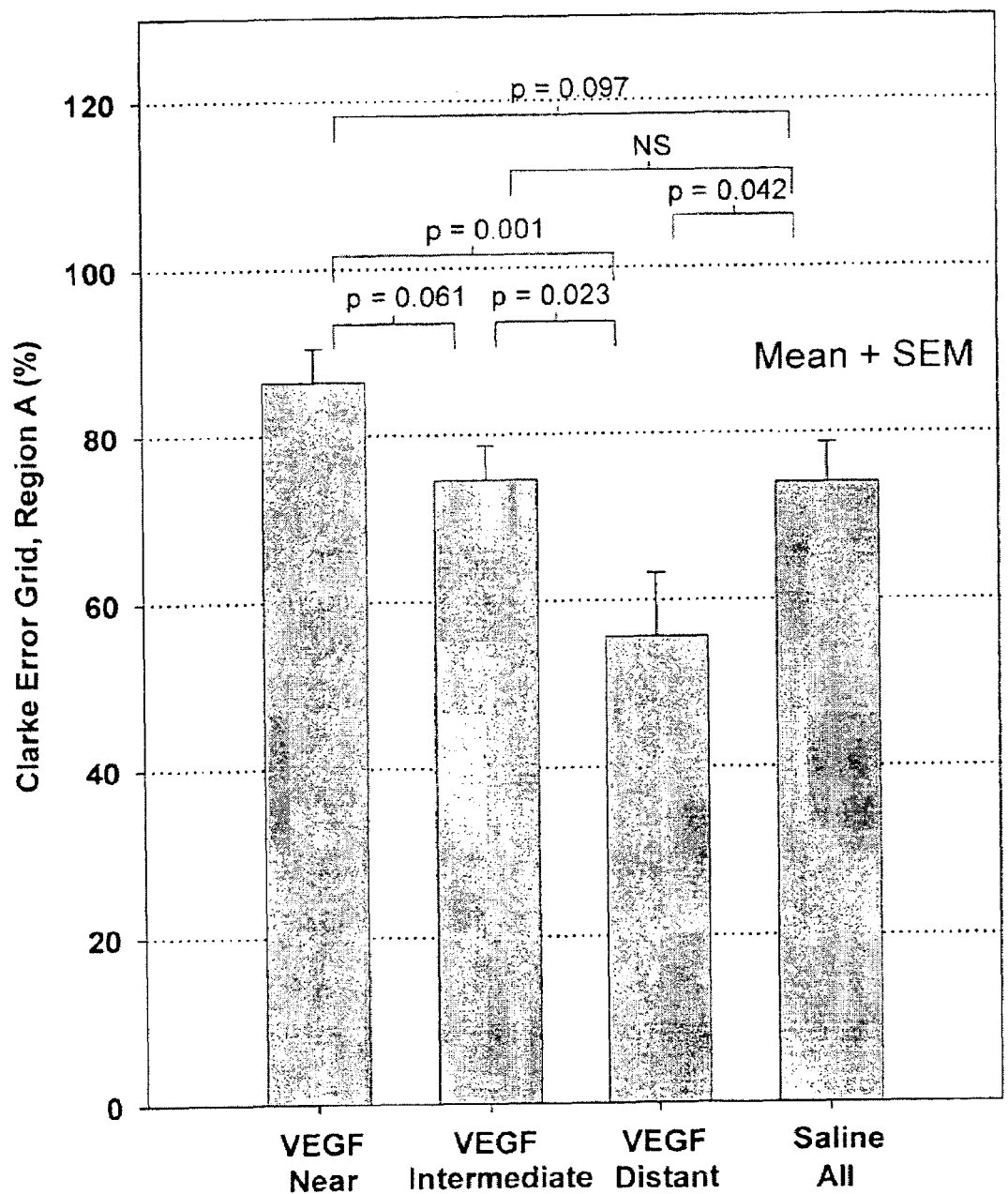
Figure 5:
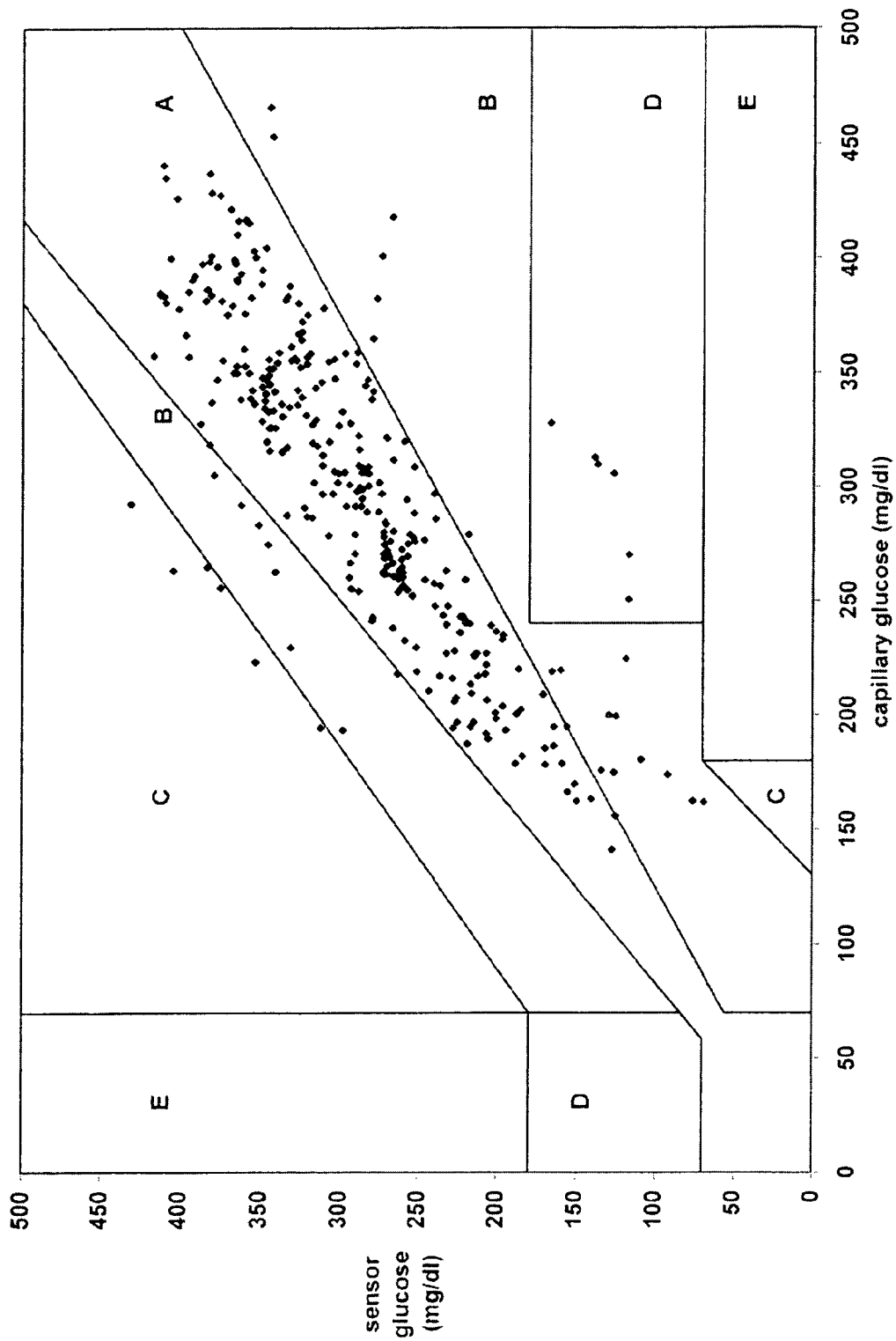

We have invented an implantable system for sensing analytes designed to accurately function for long periods of time. In addition to the primary use, this design could easily serve in a non-implanted application.

Other Uses of the Sensor System

With minor modifications, the following sensor design can detect analytes other than glucose. Covering the indicating (sensing) electrodes with other enzymes and slightly altering the polyurethane can make the sensor capable of measuring many other compounds. Examples of other analytes measured by the described sensor design include but are not limited to lactate, I-methionine, I-phenylalanine, d-aspartate, d-glutamate, urate, ethyl alcohol, methyl alcohol, cholesterol, ascorbic acid, and many others.

The described sensor design can also be used to measure concentrations in other fluids other than bodily fluids. Examples of other fluids include but are not limited to fruit and vegetable juices, wine, yogurt, and many others.

The following description relates primarily to the implantable glucose sensing system.

Construction of an Implantable Glucose Sensor

Each sensor is comprised of multiple (for example, four) sensing units (indicating electrodes) enclosed in a single epoxy housing. Multiple (for example, four) platinum indicating (sensing) electrodes are precision-cut and mounted equidistant from each other on the perimeter of the bottom planar surface of the housing. A silver reference electrode is centrally mounted, thus it is surrounded by the indicating (sensing) electrodes. The multiple platinum and the single silver electrodes are permanently bonded into position with epoxy resin.

The planar surface is sanded with fine sandpaper to achieve a consistently smooth, flat surface. The silver electrode is then scored repeatedly (by a manual process of by using a laser beam to create channels) in order to increase its surface area. The sensor is then gas plasma-etched to remove residue and increase surface adhesion. The sensor is then processed in an ultrasonicator with a solution of isopropanol, acetone, and deionized water.

Once the processing is completed, the reference electrode is polarized in a solution of KCl to deposit a layer of silver chloride. The indicating (sensing) electrodes are then covered by a glucose oxidase hydrogel solution consisting of 140-mg glucose oxidase and 41-mg bovine serum albumin dissolved in 1 mL of deionized water mixed 23:1 with glutaraldehyde. After drying, the unreacted glutaraldehyde is removed by soaking in deionized water.

Once the sensor is dried, a loop coating solution is prepared from a selectively permeable polyurethane dissolved in dimethylacetamide (DMAC). A wire loop is dipped into the solution to create a meniscus and then lowered over the planar surface of the sensor. The sensor is then cured in a laboratory oven. After oven curing, the sensor is soaked in deionized water for a period of five days to rid the sensor of any residual DMAC.

In Vitro Testing of an Implantable Glucose Sensor

The sensor is polarized at 0.6 V and allowed to settle in phosphate-buffered saline (PBS), pH 7.4. Once stable, the sensor is tested in ascending standards of glucose. An implant-grade sensor has a response time of less than two minutes, has sensitivity greater than two nano-amperes per milli-molar of glucose, and is predominantly linear in terms of its response to glucose over a glucose concentration from 0-20 mM. If a sensor meets all the previous criteria, it is fitted with a multi-channel (for example, four channel) transmitter, hermetically sealed, and implanted.

In Vivo Manipulations and Adjustments

One of the primary reasons for an implanted sensor to eventually lose its ability to measure the concentration of an analyte of interest is a collagenous foreign body capsule (FBC). The FBC surrounding the sensor eventually loses its vascularity and becomes thick and fibrous. Due to reduced circulation around the sensor, the analyte of interest can no longer be monitored.

Shults, Updike and associates observed that a double layer of expanded poly-tetrafluoroethylene (ePTFE) serves to enhance sensor function over the long term (U.S. Pat. No. 6,001,067, issued Dec. 14, 1999). This patent teaches a device for measuring glucose in a biological fluid that employs both a bioprotective membrane and an angiogenic layer, said angiogenic layer positioned more distal to the sensor housing than the bioprotective membrane. These workers found that such a double membrane system increases the capillaries that grow into the foreign body capsule that forms around a chronically implanted glucose sensor and that such growth increases the longevity of such devices (Updike, Shults et al.

2000). The effective pore size of the bioprotective membrane is 0.1 micron to about 1.0 micron.

In contrast to Shults et al, we have studied the use of a single layer of porous membrane (with a single effective pore size). This single membrane creates an appropriate structure for biological tissues to grow into while minimizing the permeation distance for the analyte of interest. In addition to supplying a growth structure, the membrane also filters out many kinds of cells that deter sensor success. By enclosing the sensor in a single layer of a porous material that minimizes tissue reaction, such as ePTFE or poly-vinyl alcohol sponge membrane, the sensor can functionally survive for long periods of time. Also, a small pore size material blocks some of the cells that serve to form the FBC. We have studied rats during long term implants. Some of the animals had sensors enclosed in a single layer of ePTFE and others had sensors enclosed in PVA sponge membrane. Others had no surrounding membrane around their sensor (controls). In terms of histologic analysis obtained at 4-6 weeks, we observed that the ePTFE and the PVA led to a growth of multiple capillaries into the foreign body capsule that surrounded the sensor. The control animals had a paucity of capillaries in their foreign body capsule. (Ward W K, Slobodzian E P et al. 2002). The effective pore size for the ePTFE that we have found to be effective is 0.1-5 microns, most preferably 0.5-2 microns. Such membranes are widely available such as from the Millipore Corporation.

Another method of improving the functional life of an implanted sensor is to release angiogenic cytokines such as Angiopoietin-1. By releasing this cytokine, the vasculature forming around the sensor in response to wound healing can be nurtured and matured instead of degraded. A localized release, instead of a more systemic application, insures that the desired effects are only created around the sensor, specifically around the indicating (sensing) electrodes. Also, through the controlled release of a biodegradable matrix, pump, or other controlled drug release system, precise amounts of angiopoetin-1 can be released into specific locations allowing for the controlled growth of blood vessels around the indicating (sensing) electrodes.

The local administration of a factor promoting angiogenesis of the FBC or of factors that attenuate FBC formation can be accomplished in the following manner. Using aseptic technique, an Alzet mini-osmotic pump (Model 2004, 250 □L capacity 28 day duration) is filled with a solution of the inhibiting factor (the desired dose is dissolved in PBS with 0.6% BSA, pH 7.4) which has been sterile filtered. The PE-50 tube attached to the sensor is filled with saline, and the pump is fitted to the tube. The sensor/pump assembly is placed in a sterile dish and covered with 0.9% saline, which is incubated at 37° C. for 40 hours before implantation.

An alternate method of local release of FBC inhibitors is by means of a PLGA microsphere matrix. Initially, 500 mg of 65/35 poly (DL-lactide-co-glycolide) and 5 mg polyethylene glycol is dissolved in 2 ml of methylene chloride by vortexing vigorously. To this solution is added 100 mg bovine serum albumin (BSA) and the desired dose of the inhibiting factor being administered; these are vortexed at a medium-high setting for thirty seconds. To the inhibitor/polymer solution is added 10 mL of 0.3% (w/v) polyvinyl alcohol (PVA) in de-ionized $H_2O$ and vortexed at a medium-high setting for an additional thirty seconds. To extract the microspheres now formed, 90 mL 0.3% PVA and 100 mL 2% isopropyl alcohol (IPA) is added to the emulsion and continuously stirred for 90 minutes at room temperature. To isolate the microspheres, the microsphere solution is centrifuged at 200×g for 10 minutes. The solution is titred off, and to this solution is added 200 mL fresh de-ionized $H_2O$. The new solution is centrifuged as before. This washing step is repeated. Remaining liquid is removed taking care not to disturb the microspheres. The microspheres are frozen to −80° C., then lyophilized. These microspheres are then fixed in a groove proximal to the indicating platinum electrodes.

Instead of working with an existing FBC, cytokines can be manipulated to block the immune response to the sensor. The attempt of the body to isolate the implanted sensor proceeds along a specific biochemical pathway. Fibrosis is likely initiated by binding of proteins such as fibrinogen to a foreign body such as our sensor. (Katou, Ohtani et al. 1998) Macrophages recognize and attach to the fibrinogen, (O'Connor, Patuto et al. 1997; Hu, Eaton et al. 2001) secreting cytokines including Angiotensin Converting Enzyme (ACE), which promotes the conversion of Angiotensin to Angiotensin II. Angiotensin II encourages fibrogenic effects through the up-regulation of TGF-β, as well as increased fibroblast TGF-β receptor expression, in renal fibroblasts. (Wolf, Ziyadeh et al. 1995) Recruited fibroblasts undergo phenotypic changes to become myofibroblasts under the influence of TGF-β, marked by increased smooth muscle actin and autocrine TGF-β expression. (Khouw, van Wachem et al. 1999) TGF-β activates the intracellular kinase activity of its receptor, which phosphorylates Smad proteins; these proteins regulate DNA transcription of collagen type I in fibroblasts. (Roberts, Piek et al. 2001) After the protein has been produced, but before it has achieved its final form, prolyl-4-hydroxylase enzymes modify proline resides on the procollagen molecule, which allow it to form a triple-helical structure formed of three collagen fibers. The collagen then becomes deposited around the sensor and accumulates. Over time the dense capsule blocks the diffusion analytes by increasing the distance over which they must diffuse from the capillary network to the sensing electrodes.

The formation of a dense foreign body capsule can be effectively inhibited, blocked or retarded by the systemic or local delivery of a number of compounds that affect one or more biological steps during which mature collagen is formed. These compounds are listed in the claims.

The use of redundancy and real-time statistical processing reduces the occurrence of error through outlier exclusion by means of the ZMAD technique. Due to differing conditions and differences in position, sensors are bound to vary in accuracy from time to time. By having multiple sensing units placed equidistant from one another, variations in one indicating (sensing) electrode can be seen by comparing it to the other electrodes. These variations can then be filtered out before a median is calculated. Through this process, the final single stream of real-time data shows greater accuracy.

The median-based ZMAD technique (and its comparison in an animal study to a mean-based technique) is described in more detail as follows: Data were obtained from disk arrays (which contained 4 sensing units) that were implanted under the skin in rats. Data were analyzed in two ways, and both of these ways can be used in real time. The first method was a classic signal averaging method in which the calibrated sensor glucose values for all four channels were averaged. The second method ("ZMAD processing method") was designed to exclude data from any anode sensing unit whose data was inconsistent with the other units.

The protocol for data exclusion using ZMAD utilized a Median Absolute Deviation (MAD) with a Z-score for each simultaneous data set (Rousseeuw 1990) Specifically, the data processing algorithm utilized a modified Z-score calculated for each data set (obtained once per minute) from each of the four sensing anode units. For a given sensing unit (unit X), at a given time point, a Z score was calculated based on calibrated sensor glucose values (SG):

$$Z \text{ score} = \frac{|deviation_{unit\ X}|}{|\text{Median of all deviations}| * 1.483}$$

With the numerator more specifically defined, the formula can be restated as:

$$Z \text{ score} = \frac{|\text{Median } SG_{all\ units} - SG_{unit\ X}|}{|\text{Median of all deviations}| * 1.483}$$

The constant 1.483 is a correction factor designed to make the estimator scale factor consistent with the usual scale parameter of a normal distribution (Rousseeuw 1990) Z-score channel values of greater than 1 were excluded as outliers and the final reading given for a particular array at a given time was then computed as the mean of the remaining channels.

The results indicated that use of the ZMAD technique led to very accurate sensing when blood glucose (measured independently from blood samples taken from the animal) was used as a standard. Using ZMAD, 97-98% of the data pairs (blood glucose and sensor glucose) fell in the A and B regions of the Clarke Error Grid, a plot widely used to assess accuracy of glucose monitoring methods. The signal averaging method was substantially less accurate that the ZMAD technique.

A Z-score can be generally computed as follows:

$$Z_i = \frac{x_i - \text{location } T}{\text{scale } S}$$

$Z_i$ is referred to as a Z-score and may be used to identify outlier data. $x_i$ is a data point of a sample being measured. Location T measures the general position of the sample data being measured. Location T may be the median, mean, or any other desired robust or non-robust estimator of the sample being measured. Scale S estimates the scale or spread of the sample being measured. Scale S may be the standard deviation, or the median of all absolute deviations (MAD) from the sample median. As a general principle, outliers can be identified by comparing data with a robust fit.

The following numbered paragraphs illustrate without limitation further aspects of the invention:

1. An implantable device for animals or humans that measures an analyte in a biological fluid by use of an oxidoreductase enzyme that has multiple sensing (indicating) electrodes and one or more reference electrodes.
2. The device of paragraph 1 where the sensing electrodes are positioned on one or both sides of a planar or convex surface.
3. The device of paragraph 1 wherein said sensing (indicating) electrodes comprise three or more sensing (indicating) electrodes composed of platinum, gold, palladium or carbon.
4. The analyte measuring device of paragraph 1, wherein said device is composed of plastic, glass, insulated metal, or any other dielectric material shaped in a circular, spherical, oval, square, T, or triangular fashion with rounded or lozenge-shaped edges.
5. The analyte measuring device of paragraph 1, wherein said sensing (indicating) electrodes utilize oxidase or dehydrogenase enzyme-mediated amperometric measurement of analyte wherein said oxidase or dehydrogenase is glucose oxidase or glucose dehydrogenase
6. The analyte measuring device of paragraph 1, wherein said sensing (indicating) electrodes utilize a permselective membrane
7. The device of paragraph 6 wherein said membrane is composed of a polyurethane.
8. The device of paragraph 1 with an outermost single-layered porous membrane covering the sensing surface(s) or entire device.
9. The analyte measuring device of paragraph 2, wherein said membrane is composed of a porous polymer.
10. The analyte measuring device of paragraph 2, wherein said membrane is expanded in either one or multiple directions further comprising pores having diameters ranging from 0.5 micron to 3.0 micron.
11. The analyte measuring device of paragraph 2, wherein said membrane is composed of polymers including, but not limited to, poly-tetraflouroethylene or poly vinyl alcohol.
12. The device of paragraph 1 where angiopoetin-1 is delivered (locally, near the implanted sensor, or systemically) in order to create new capillary formation in the foreign body capsule (in a dose of 1 pg-1 mg/day released over 1-180 days; most preferably 3 ng-3 μg/day for at least 4 weeks).
13. The analyte measuring device of paragraph 12 wherein said angiopoetin-1 is contained in a pump or in a matrix such as poly-lactic-glycolic acid incorporated into the analyte measuring device of claim 1 that slowly releases its contents over time.
14. The analyte-measuring device of paragraph 12, wherein said angiopoetin-1 is released in close proximity to the sensing (indicating) electrodes.
15. The analyte measuring device of paragraph 12, wherein said angiopoetin-1 is released from a pore or channel within zero to fifteen millimeters of said sensing (indicating) electrodes of paragraph 1.
16. Use of data obtained from at least two channels from the device of paragraph 1 to produce a single unified signal that is displayed to the user in real time.
17. Data processing of paragraph 16, wherein said processing includes the use of the arithmetic mean.
18. The processing of paragraph 16, wherein said processing more preferably includes the use of the median.
19. The processing of paragraph 16, wherein said processing includes most preferably the use of the ZMAD statistic (Z-statistic, Median of Absolute Deviations) wherein ZMAD utilizes a modified Z-score calculated for each data set allowing for the real-time rejection of outlying signals accompanied by consolidation of remaining signals into a single signal by use of a mean or median calculation of those remaining signals.
20. The device of paragraph 1 wherein a chemical designed to block the formation of the fibrous foreign body capsule is released locally.
21. The device of paragraph 20 where such a chemical inhibits a step in the biosynthesis of collagen or a step in the post-translational modification of collagen.
22. The device of paragraph 21 where such a chemical is halofuginone (a dose of 1 pg-1 mg/kg/day is effective when released over 1-180 days; ideal dose of 3.5 μg/kg/day for 28 days,).

23. The device of paragraph 21 where such a chemical is mimosine (a dose of 1 pg-100 mg/kg/day is effective when released over 1-180 days; ideal dose of 10 mg/kg/day for 28 days).

24. The device of paragraph 21 where such a chemical is pirfenidone (a dose of 1 pg-50 mg/kg/day is effective when released over 1-180 days; ideal dose of 7 mg/kg/day for 28 days).

25. The device of paragraph 21 where such a chemical is ethyl 3,4-dihydroxybenzoate (a dose of 1 pg-50 mg/kg/day is effective when released over 1-180 days; ideal dose of 7 mg/kg/day for 28 days).

26. The device of paragraph 21 where such a chemical is dimethyloxalylglycine (a dose of 1 pg-50 mg/kg/day is effective when released over 1-180 days, ideal dose of 1 mg/kg/day for 28 days).

27. The device of paragraph 20 where such a chemical inhibits the synthesis or action of Transforming Growth Factor Beta (TGF-beta).

28. The device of paragraph 27 wherein such a chemical consists of pirfenidone (a dose of 1 pg-50 mg/kg/day is effective when released over 1-180 days; ideal dose of 7 mg/kg/day for 28 days).

29. The device of paragraph 27 wherein such a chemical consists of decorin (a dose of 1 pg-50 mg/kg/day is effective when released over 1-180 days; ideal dose of 400 µg/kg/day for 28 days).

30. The device of paragraph 27 wherein such a chemical consists of halofuginone (a dose of 1 pg-50 mg/kg/day is effective when released over 1-180 days; ideal dose of 34.2 µg/kg/day for 28 days).

31. The device of paragraph 27 wherein such a chemical consists of interferon gamma (a dose of 1 pg-50 mg/kg/day is effective when released over 1-180 days; ideal dose of 15 mU/kg/day for 28 days).

32. The device of paragraph 27 wherein such a chemical consists of an angiotensin converting enzyme inhibitor (a dose of 1 pg-100 mg/day is effective when released over 1-180 days; ideal dose of 16 mg/kg/day for 28 days).

33. The device of paragraph 27 wherein such a chemical consists of an angiotensin II receptor blocker (such as valsartan, losartan, irbesartan or others in this class) in a dose of 1 pg-50 mg/kg/day released over 1-180 days; an ideal dose is 1.0 mg/kg/day for 28 days).

34. The device of paragraphs 21 or 27 wherein said biochemicals are contained in a matrix or pump incorporated into the analyte measuring device of paragraph 1 that slowly releases its contents over time.

35. The analyte measuring device of paragraphs 21 or 27, wherein said biochemicals are released in close proximity to the sensing (indicating) electrodes.

36. The analyte measuring device of paragraphs 21 of 27, wherein said biochemicals are released from a site zero to fifteen millimeters of said sensing (indicating) electrodes of paragraph 1.

The specific embodiments disclosed and illustrated herein should not be considered as limiting the scope of the invention, as understood by a person having ordinary skill in the art. Numerous variations are possible without falling outside the scope of the appended claims. The subject matter of the invention includes all novel and nonobvious combinations and subcombinations of the various elements, features, functions, and/or properties disclosed herein.

We claim:

1. A system for monitoring analyte levels in an individual comprising
    an implantable biosensor that uses an oxidoreductase enzyme and has multiple electrodes, and
    a processor that receives signals from the electrodes, excludes outlying signals based on a statistical median analysis, and calculates a mean or median from the remaining signals, wherein the statistical median analysis uses a Z-statistic, Median of Absolute Deviations.

2. A system for monitoring analyte levels in an individual comprising
    an implantable biosensor that uses an oxidoreductase enzyme and has multiple electrodes, and
    a processor that receives signals from the electrodes, excludes outlying signals based on a statistical median analysis, and calculates a mean or median from the remaining signals, wherein each electrode generates a sensor glucose value (SG), outlier exclusion being determined based on a Z score calculated for each sensor at a given time, the Z score being calculated according to the following formula:

$$Z\text{ score} = \frac{|\text{Median } SG_{all\,units} - SG_{unit\,X}|}{|\text{Median of all deviations}| * 1.483}.$$

3. The system of claim 2, wherein the processor calculates a mean from the remaining SG values after excluding outliers.

4. The system of claim 2, wherein an SG value is excluded as an outlier if it has a Z score greater than 1.

5. A system for monitoring analyte levels in an individual comprising
    an implantable biosensor that uses an oxidoreductase enzyme and has multiple electrodes, and
    a processor that receives signals from the electrodes, excludes outlying signals based on a statistical median analysis, and calculates a mean or median from the remaining signals, wherein the statistical median analysis uses a Z-score.

6. The system of claim 5, wherein the Z-score is based on the difference between a given SG value and a median SG value of all units compared to a scaled SG value of all units.

7. A system for monitoring analyte levels in an individual comprising
    an array of implantable glucose sensors, each sensor using an electrode pair and glucose oxidase to generate real time glucose sensor values (SG), and
    a processor programmed to exclude outlying SG values based on the difference between a given SG value and the median SG value of all units, wherein the processor is programmed to exclude outlying SG values based on the difference between a given SG value and the median SG value of all units divided by a scaled SG value of all units.

8. The system of claim 7, wherein the scaled SG value of all units is a median of all absolute deviations value.

9. A system for monitoring analyte levels in an individual comprising
    an array of implantable glucose sensors, each sensor using an electrode pair and glucose oxidase to generate real time glucose sensor values (SG), and
    a processor programmed to exclude outlying SG values based on a Z-score.

10. The system of claim 9, wherein the Z-score is the difference between a given SG value and a location SG value of all units compared to a scaled SG value of all units.

11. The system of claim 10, wherein the location SG value of all units is a median SG value of all units.

12. The system of claim 10, wherein the scaled SG value of all units is a median of all absolute deviations value.

* * * * *